US00PP28869P2

(12) United States Plant Patent
Taquet

(10) Patent No.: US PP28,869 P2
(45) Date of Patent: Jan. 9, 2018

(54) ***PENSTEMON* PLANT NAMED 'CHERRY SPARKS'**

(50) Latin Name: ***Penstemon* hybrid**
Varietal Denomination: Cherry Sparks

(71) Applicant: Ball Horticultural Company, West Chicago, IL (US)

(72) Inventor: Valentin Taquet, Amsterdam (NL)

(73) Assignee: Ball Horticultural Company, West Chicago, IL (US)

( * ) Notice: Subject to any disclaimer, the term of this patent is extended or adjusted under 35 U.S.C. 154(b) by 9 days.

(21) Appl. No.: 15/330,160

(22) Filed: Aug. 16, 2016

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Susan McCormick Ewoldt
(74) *Attorney, Agent, or Firm* — Audrey Charles

(57) ABSTRACT

A new and distinct cultivar of *Penstemon* plant named 'Cherry Sparks', characterized by its red-colored flowers, having white coloration at the throat, medium green-colored foliage, and moderately vigorous, upright growth habit, is disclosed.

1 Drawing Sheet

Latin name of genus and species of plant claimed: *Penstemon* hybrid.

Variety denomination: 'Cherry Sparks'.

BACKGROUND OF THE INVENTION

The present invention relates to a new and distinct cultivar of *Penstemon* plant botanically known as *Penstemon* hybrid and hereinafter referred to by the cultivar name 'Cherry Sparks'.

The new cultivar originated in a controlled breeding program in Venhuizen, the Netherlands during August 2012. The objective of the breeding program was the development of *Penstemon* cultivars having large flowers and a long flowering season.

The new *Penstemon* cultivar was the result of a self-pollination of 'Andenken an Friedrich Hahn' syn. 'Garnet', not patented, characterized by its garnet-red colored flowers, medium green-colored foliage, and vigorous, upright growth habit. The new cultivar was discovered and selected as a single flowering plant within the progeny of the above stated self-pollination during July 2013 in a controlled environment in Venhuizen, the Netherlands.

Asexual reproduction of the new cultivar by terminal stem cuttings since July 2013 in Venhuizen, the Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Cherry Sparks' as a new and distinct cultivar of *Penstemon* plant:

1. Red-colored flowers, having white coloration at the throat;
2. Medium green-colored foliage; and
3. Moderately vigorous, upright growth habit.

Plants of the new cultivar differ from plants of the parent primarily in having reduced growth vigor and a white-colored throat.

Of the many commercially available *Penstemon* cultivars, the most similar in comparison to the new cultivar is 'Red Riding Hood', U.S. Plant Pat. No. 18,950. However, in side by side comparisons, plants of the new cultivar differ from plants of 'Red Riding Hood' in at least the following characteristics:

1. Plants of the new cultivar have larger flowers than plants of 'Red Riding Hood';
2. Plants of the new cultivar have a flower color different from plants of 'Red Riding Hood'; and
3. Plants of the new cultivar have a longer blooming season than plants of 'Red Riding Hood'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Cherry Sparks'. The plants were approximately seven-months old and grown in one-gallon containers in a greenhouse in Elburn, Ill. Plants were given one pinch prior to transplant and one pinch two weeks after transplant.

DETAILED BOTANICAL DESCRIPTION

Figure 1:
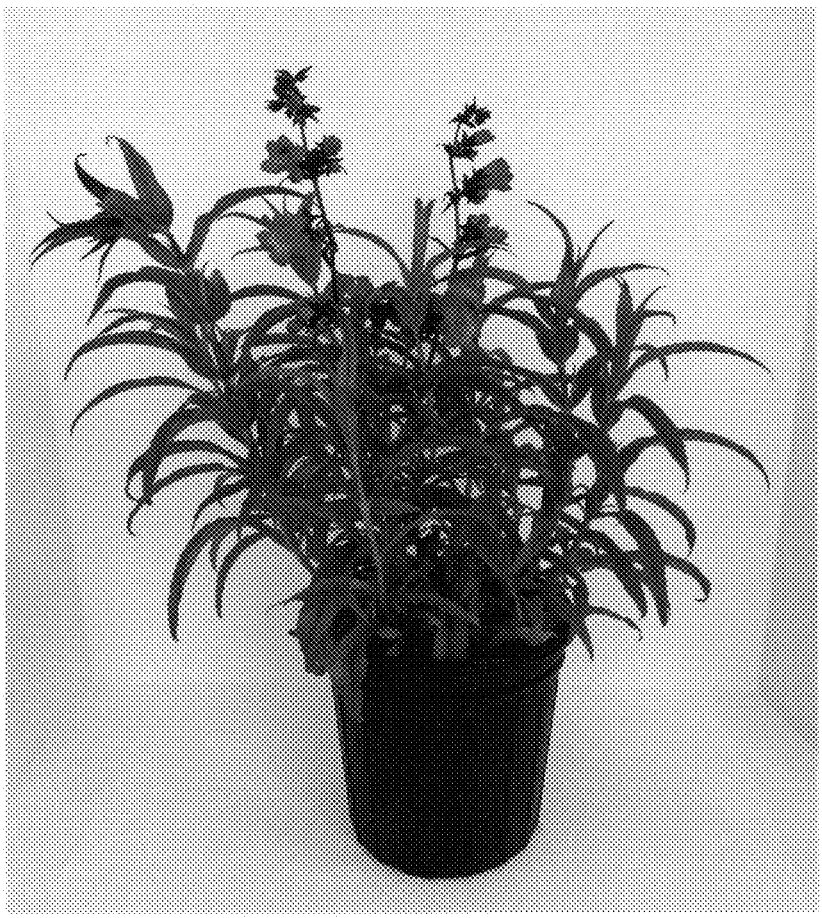
FIG. 1 illustrates a side view of the overall growth and flowering habit of 'Cherry Sparks'.
Figure 2:
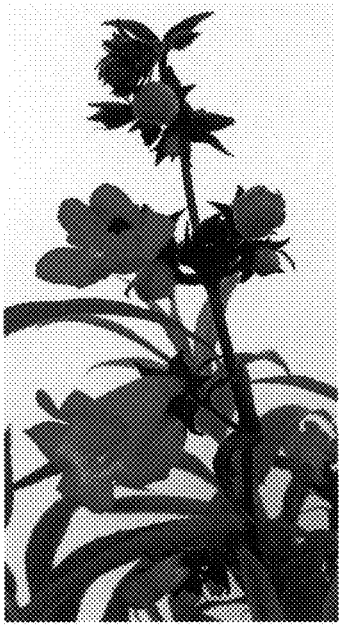
FIG. 2 illustrates a close-up view of an inflorescence of 'Cherry Sparks'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2016 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in one-gallon containers for approximately seven months in Elburn, Ill. Plants were transplanted in late fall from rooted cuttings and were given one pinch prior to transplant and one pinch two weeks after transplant. Greenhouse temperatures were maintained during the winter months at approximately 45° F. to 65° F. (7.2° C. to 18.3° C.) during the day and approximately 35° F. to 45° F. (1.7° C. to 7.2° C.) during the night. For the final 9 weeks, greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Penstemon* hybrid cultivar Cherry Sparks.

Parentage:

*Parent*.—'Andenken an Friedrich Hahn' syn. 'Garnet', not patented.

Propagation:

*Type cutting*.—Terminal stem.

*Time to initiate roots*.—Approximately 10 to 12 days.

*Time to produce a rooted cutting*.—Approximately 5 to 6 weeks.

*Root description*.—Fine to medium, fibrous white to light brown in color.

*Rooting habit*.—Freely branching.

Plant description:

*Commercial crop time*.—Approximately 10 to 12 weeks from a rooted cutting to finish in a 15 cm pot.

*Growth habit and general appearance*.—Perennial; moderately vigorous, upright growth habit.

*Hardiness*.—USDA Zones 5 to 9.

*Size*.—Height from soil level to top of plant plane: Approximately 42.0 cm. Width: Approximately 40.0 cm.

*Branching habit*.—Freely branching. Pinching enhances lateral branching. Quantity of branches per plant: Approximately 11.

*Branch*.—Shape: Round in cross section. Strength: Strong. Length: Approximately 33.0 cm. Diameter: Approximately 5.0 mm. Length of central internode: Approximately 3.0 cm. Texture: Densely pubescent with very short hairs. Color of young stem: 145B. Color of mature stem: 145A with an overlay of 187A.

Foliage description:

*General description*.—Quantity of leaves per branch: Approximately 18. Fragrance: None detected. Form: Simple. Arrangement: Opposite and decussate.

*Leaves*.—Aspect: Acute angle to stem with tips downward turning. Shape: Linear. Margin: Serrate. Apex: Acute. Base: Sessile. Venation pattern: Pinnate. Length of mature leaf: Approximately 12.0 cm. Width of mature leaf: Approximately 1.7 cm. Texture of upper and lower surfaces: Glabrous. Color of upper surface of young and mature foliage: 137B with venation of 146D. Color of lower surface of young and mature foliage: Closest to 146B with venation of 146D.

Flowering description:

*Flowering habit*.—'Cherry Sparks' is freely flowering under outdoor growing conditions blooming from late spring through late summer.

*Lastingness of individual floret*.—Approximately 6 to 7 days.

Inflorescence description:

*General description*.—Type: Terminal and axillary racemes, flowers face outward. Quantity of open inflorescences per plant: Approximately 4. Fragrance: None detected. Length or height of inflorescence: Approximately 17.0 cm. Width of inflorescence: Approximately 7.0 cm. Quantity of fully-open flowers per inflorescence: Approximately 9.

*Peduncle*.—Strength: Strong. Aspect: Erect. Length: Approximately 4.5 cm. Diameter: Approximately 3.0 mm. Texture: Densely glandular pubescent. Gland color: Colorless, transparent. Color: 145A with a heavy overlay of 187A.

Flower description:

*Type*.—Single, zygomorphic.

*Bud*.—Rate of opening: Generally takes 3 to 4 days for bud to progress from first color to fully open flower.

*Bud just before opening*.—Shape: Obovoid. Length: Approximately 1.5 cm. Diameter: Approximately 7.0 mm. Texture: Densely glandular pubescent. Gland color: Colorless, transparent. Color: Calyx of 145A with a heavy overlay of 187A, margins of 202A; petals of 145D with apex of 53C to 53D.

*Corolla*.—Shape: Bilabiate, upper lip of two lobes and lower lip having three lobes. Width: Approximately 3.1 cm. Length: Approximately 3.0 cm. Depth: Approximately 3.5 cm.

*Upper lip lobes*.—Shape: Ovate. Margin: Entire. Apex: Broadly acute. Length from throat: Approximately 8.0 mm. Width: Approximately 1.0 cm. Texture of upper and lower surfaces: Glabrous. Color of upper surface when first and fully open: 53C to 53D. Color of lower surface when first and fully open: 53D.

*Lower lip lobes*.—Shape: Ovate. Margin: Entire. Apex: Broadly acute. Length from throat of central lobe: Approximately 1.0 cm. Width of central lobe: Approximately 1.2 cm. Length from throat of lateral lobes: Approximately 1.0 cm. Width of lateral lobes: Approximately 1.3 cm. Texture of upper and lower surfaces: Glabrous. Color of upper surface when first and fully open: 53C to 53D. Color of lower surface when first and fully open: 53D.

*Corolla tube*.—Length: Approximately 3.0 cm. Width: Approximately 1.3 cm. Texture of inner surface: Glabrous. Texture of outer surface: Moderately pubescent. Color of inner surface: NN155D with venation of 71A. Color of outer surface: 53D with NN155D at base.

*Calyx*.—Shape: Star. Length: Approximately 1.2 cm. Diameter: Approximately 1.6 cm.

*Sepals*.—Quantity per flower: 5. Apex: Acute. Base: Truncate. Length: Approximately 1.2 cm. Width:

Approximately 5.0 mm. Texture of inner surface: Sparsely glandular pubescent. Texture of outer surface: Densely glandular pubescent. Gland color: Colorless, transparent. Color of inner surface: 145A with an overlay of 187A on upper half. Color of outer surface: 187A.

*Pedicel*.—Strength: Strong, flexible. Aspect: At an acute angle. Length: Approximately 5.0 mm. Diameter: Approximately 1.0 mm. Texture: Densely glandular pubescent. Gland color: Colorless, transparent. Color: 187A.

*Reproductive organs*.—Androecium: Stamen quantity: 5 per flower, one lacking an anther, connate by filaments. Stamen length: Approximately 2.7 cm. Filament length: Approximately 2.5 cm. Filament length of fixed portion: Approximately 7.0 mm. Filament color: NN155D, opaque with an overlay of 71A. Anther shape: Horseshoe-like. Anther length: Approximately 3.0 mm. Anther color: N92D. Pollen amount: Abundant. Pollen color: NN155D. Gynoecium: Pistil quantity: 1 per flower. Pistil length: Approximately 2.4 cm. Stigma shape: Conical. Stigma length: Less than 1.0 mm. Stigma color: NN155D. Style length: Approximately 2.0 cm. Style color: NN155D with a faint overlay of 71D. Ovary length: Approximately 4.0 mm. Ovary color: N144D.

Seed and fruit production: Neither seed nor fruit production has been observed.

Disease and pest resistance: Resistance to pathogens and pests common to *Penstemon* has not been observed.

What is claimed is:

1. A new and distinct cultivar of *Penstemon* plant named 'Cherry Sparks', substantially as herein illustrated and described.

* * * * *